United States Patent [19]

Brode et al.

[11] 4,433,119

[45] Feb. 21, 1984

[54] LIQUID THERMOSETTING COMPOSITIONS CONTAINING HEMIFORMALS OF PHENOL

[75] Inventors: George L. Brode; Sui-Wu Chow, both of Bridgewater Township, Somerville County, N.J.

[73] Assignee: Union Carbide Corporation, Danbury, Conn.

[21] Appl. No.: 340,720

[22] Filed: Jan. 19, 1982

[51] Int. Cl.³ .................... C08G 61/10; C08G 61/14; C08G 67/06; C08G 69/00

[52] U.S. Cl. .................................. 525/442; 425/543; 525/462; 525/465; 525/480; 525/488; 525/497; 525/498; 525/500; 525/501; 525/502; 525/503; 525/521; 528/139; 528/140; 528/165; 528/254

[58] Field of Search ............... 525/462, 465, 442, 497, 525/498, 480, 488, 500, 501, 503, 502, 521; 528/165, 254; 425/543

[56] References Cited

U.S. PATENT DOCUMENTS

| | | | |
|---|---|---|---|
| 2,609,352 | 9/1952 | Kvalnes | 260/45.1 |
| 2,894,931 | 7/1959 | Somerville et al. | 260/43 |
| 3,062,783 | 11/1962 | Gray et al. | 260/49 |
| 3,485,797 | 12/1969 | Robins | 260/57 |
| 3,624,035 | 11/1971 | von Portatius | 528/254 X |
| 3,959,433 | 5/1976 | Sauers | 264/328 |
| 4,022,942 | 5/1977 | Anderson et al. | 427/393 |

FOREIGN PATENT DOCUMENTS 667360 11/1965 Belgium .
1107244 3/1968 United Kingdom .

OTHER PUBLICATIONS

Strupinskaya et al., Plast. Massy., 1968, pp. 18–20, Translation (pp. 21–23) Supplied by Applicant.
Walker, Formaldehyde, 3rd Edition, Reinhold Publishing Corp., New York (1964), pp. 305–306.
Bakeland and Bender "Industrial and Engineering Chemistry," vol. 17, No. 3, pp. 225–237 (1925).

*Primary Examiner*—Howard E. Schain
*Attorney, Agent, or Firm*—James L. Sonntag

[57] ABSTRACT

There are described liquid compositions of a hemiformal of phenol and/or a hemiformal of a methylolated phenol with a miscible polymers such as phenol-formaldehyde resoles, phenol-formaldehyde, novolacs, aromatic polyesters, unsaturated polyesters, poly(arylethers), aromatic polycarbonates urea-formaldehyde resins, or melamine-formaldehyde resins. The compositions are useful for forming thermoset plastic materials.

11 Claims, No Drawings

LIQUID THERMOSETTING COMPOSITIONS CONTAINING HEMIFORMALS OF PHENOL

This application contains subject matter disclosed in United States Patent Application Ser. Number 242,995 filed Mar. 12, 1981, now abandoned in favor of continuation-in-part U.S. patent application, Ser. No. 340,695, filed Jan. 19, 1982.

This invention is directed to polymerizable liquid compositions containing hemiformals of phenols and other polymers that form solutions with the hemiformals. These compositions are curable to form solid resins and can be used to form composites having good physical properties.

Until recently, liquid hemiformal compositions of phenol have been unknown although there has been speculation in the literature about hemiformals of phenol for some time.

Illustrative of such literature is Walker, FORMALDEHYDE, 3rd Edition, published by Reinhold, Publishing Corporation, New York, (1964), pages 305, 306 wherein the following is stated:

"In the absence of added catalysts, anhydrous formaldehyde and paraformaldehyde dissolve in molten phenol without apparent reaction to give clear, colorless solutions which smell strongly of formaldehyde. In such solutions, it is probable that some solvation takes place and hemiformals, such as $C_6H_5OCH_2OH$, $C_6H_5OCH_2OCH_2OH$, etc., are present. However, studies of formaldehyde polymers have demonstrated that phenol is a solvent for these compounds and the majority of the dissolved formaldehyde in phenolic solutions may be in the polymerized state. Studies by Fitgerald and Martin[44] involving the measurement of hydroxyl ion concentrations in dilute, alkaline, aqueous formaldehyde in the presence and absence of the sodium phenolate of mesitol indicate that hemiformal concentrations are too small to be measured in this way. However, in our opinion hemiformal formation with a hindered phenol, such as mesitol, would be similar to hemiformal formation with tertiary butyl alcohol which does not show any appreciable solvation of formaldehyde. There is a definite analogy of nonaqueous phenol formaldehyde solutions to solutions of formaldehyde in alcohols and other polar solvents. According to Reychler[102], a small percentage of sodium phenolate catalyzes the solution of linear formaldehyde polymers in phenol, just as sodium alcoholates catalyze solution in methanol, ethanol, and other alcohols. That hemiformals are produced is also indicated by the isolation of methyl phenyl formal from an acid-catalyzed reaction of phenol with formaldehyde solution containing methanol[20].

[44.] Fitzgerald, J. S.; Martin, R. J. L., Australian J. Chem. 8, 194–214 (1955)
[102.] Reychler, A., Bull. Sot. Chim. (40) 1, p 1189–95 (1907); Chem Abs. 2, 1266 (1908)
[20.] Breslauer, J.; Pictet, A., Berichte, 40 3785 (1907)

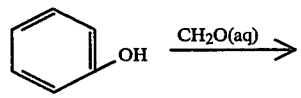

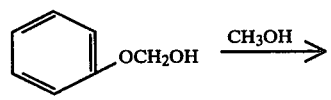

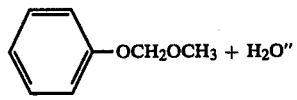

One of the difficulties with the conclusion which is raised in the Walker article is that the hemiformal is produced from an acid-catalyzed reaction of phenol with formaldehyde solution containing methanol. It is notoriously well known that acids act to catalyze the reaction of phenol with formaldehyde to effect normal alkylation of phenol by formaldehyde to produce the phenolic resins. Thus what is seen by Walker as a suggestion of the existence of the hemiformal may be nothing more than the known reaction between methanol and formaldehyde in the presence of an acid catalyst to form a product which is subsequently reacted with phenol to yield the ether product which is characterized as the final product of the reaction. Actually a reaction between formaldehyde and phenol to produce the hemiformal would have yielded an equilibrium reaction and this is totally absent from the reaction characterized by Walker; suggesting again that in the theoretical reaction disclosed by Walker the formaldehyde is first stabilized with methanol and then the product is reacted with phenol.

Bakeland and Bender in an article in "Industrial and Engineering Chemistry" Volume 17, No. 3, pages 225–237 (1925) make the following statements concerning the formation of a theoretical hemiformal of phenol:

"The phenol first unites directly with the aldehyde to form a mixed ether-alcohol compound (XXXIII), and the resulting ether group very rapidly rearranges to the phenol.

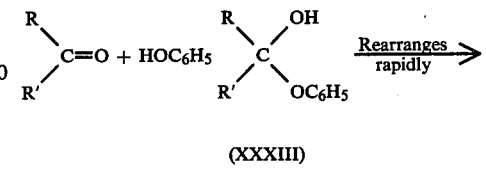

(XXXIII)

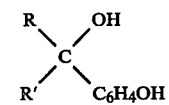

(XXXIV)

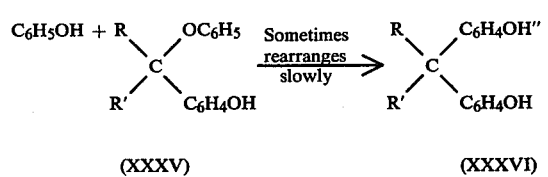

(XXXV)  (XXXVI)

Thus, Bakeland and Bender clearly indicate that if the hemiformal exists it is at best a transitory material which is unstable under the conditions at which it was produced and is a theoretical composition constituting an intermediary in the generation of phenolic resins.

Strupinskaya et al. in Plast. Massy 1968 (12), at pp 18–20 describe the preparation of a product by the absorption of formaldehyde into molten phenol at a formaldehyde to phenol ratio of 3:10. This corresponds to a formaldehyde to phenol mole ratio of 0.94:1. The source of formaldehyde was a converter gas stream containing about 10% methanol and analysis of the product showed it to contain up to 8% methanol. The presence of methanol suggests that this reference refers to a methanol stabilized product similar to that disclosed in Walker, cited above, wherein formaldehyde reacts with methanol and subsequently reacts with phenol to form the ether product. The low formaldehyde to phenol ratio also suggests that hemiformals having average formaldehyde to phenol ratios higher than 1:1 would probably not have been formed by their method.

In Belgium Patent No. 667,360 issued on November 16, 1965 to Chemische Werke Huels A.G. is disclosed the treatment of various hydroxy-compounds, including phenol, with monomeric formaldehyde, at a formaldehyde to phenol ratio of 1:1. The low formaldehyde to phenol ratio would indicate that any hemiformal formed would probably have no more than an average of one formaldehyde moiety structure in the hemiformal chain structure. As disclosed in Bakeland and Bender, cited above, hemiformals are known in the art as transitory or unstable species and would be expected by one of ordinary skill to be increasingly unstable as the length of the hemiformal chain increases. It would, therefore, be expected that additional formaldehyde added in the Huels process would react with the phenol at another site on the aromatic ring, such as at the para or orthoposition, rather than forming hemiformals with higher formaldehyde to phenol ratios. A person normally skilled in the art would, therefore, expect that hemiformal compositions having formaldehyde to phenol ratios greater than 1:1, wherein hemiformal chains having more than one formaldehyde moiety are formed, would be unstable, forming other phenol-formaldehyde resinous products or disassociating to form free formaldehyde.

The first time where it has been established that hemiformals of phenol have been made which have recognized stability are isolable, and can be utilized in the formation of a variety of products, particularly phenol-formaldehyde resins, is in United States patent applications, Ser. No. 340,719 by Covitz, Brode and Chow, and 340,790 by Brode and Chow both filed concurrently, wherein liquid hemiformal compositions of phenol produced by the reaction of formaldehyde and phenol are disclosed.

The hemiformals therein disclosed are hemiformals of phenol, and hemiformals of methylolated phenol having the formulas;

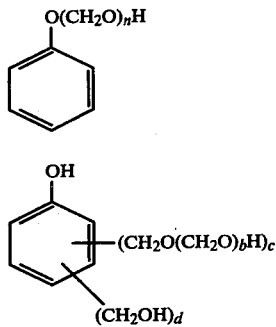

(I)

(II)

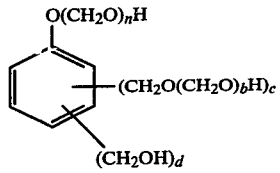

(III)

wherein n is a positive number of at least 1, preferably a value of 1 to about 5, most preferably a value of about 1.2 to 2.5; b is 1 to about 5, c is 1 to about 3, d is 0 to about 2, and the sum of c and d is at least 1 and no greater than 3.

Also disclosed are mixtures of the above hemiformals and also mixtures of any of the above with hemiformals of substituted phenols or oil modified phenols. As disclosed in the above cited applications, these hemiformals are of low viscosity and are stable at temperatures between about 35° C. and 55° C.

These hemiformal compositions are very reactive in the presence of an acid or base catalyst typically used in aldehyde-phenol polymerization reactions and are useful in forming phenolic-type resinous products.

It has now been found that the above-described hemiformal compositions can be used to form liquid solutions or thermoset compositions with other polymeric materials, that form solutions with the hemiformals, such as phenol-formaldehyde resole and novolac resins, aromatic polyester, polycarbonate, unsaturated polyester, poly(aryl ether), urea-formaldehyde, and melamine-formaldehyde polymers to form thermosetting compositions. These solutions are stable, are of low viscosity, and can be used to form thermosets and fiber reinforced composites.

These compositions are particularly useful in molding techniques such as liquid injection molding (LIM), reaction injection molding (RIM), hydrajecting, and resin transfer molding (RTM) wherein liquid thermosetting compositions are injected directly into a mold where they are cured; resulting in the formation of a fabricated part.

The compositions of the invention are also adaptable to the sheet molding compound method (SMC), wherein a resin, reinforcing fiber and other additives are mixed under low shear conditions and the resulting viscous mixture cured to non-tacky sheets. Final cure to finished parts is then carried out in a mold.

These molding processes have generally been restricted to polyesters because other types of resins, such as phenolics, have either too high a viscosity or contain excessive volatile solvents. Because of the excellent physical properties and flame resistance of phenolic resins, a composition that cures to form a phenol-formaldehyde resin and can be used in the above molding methods would be high desirable. The low viscosity phenol hemiformal and polymer compositions of the invention provide such a composition.

The thermoset compositions of the invention include mixtures of hemiformals and polymers which comprise from 40 to 80 weight percent, preferably 50 to 70 weight percent, of one or more of the hemiformals as described herein and from 20 to 60 weight percent, preferably 30 to 50 weight percent, of one or more of the polymers as described below. The percentages are based on the total weight of the composition.

The hemiformal compositions useful in the thermosetting composition of the invention can be represented by the following formulas;

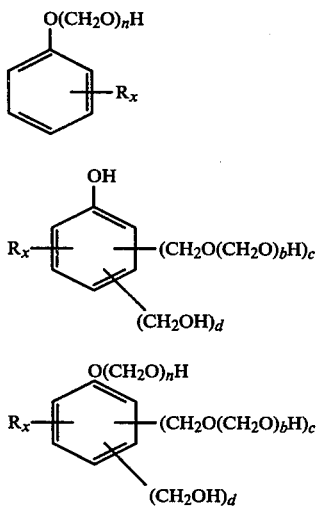

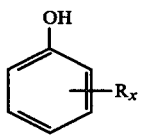

wherein n is a positive number of at least 1, preferably about 1 to about 5, most preferably about 1.2 to about 2.5. b is 1 to about 5, c is 1 to about 3, and d is 0 to about 2, x is 0 to 3, the sum of c and d is at least 1 and no greater than 3 and the sum of c, d, and x is at least 1 but no greater than 5, where x is 0 for at least 50 mole percent of the hemiformal, and with respect to the R substituent, at least 2 of the ortho- and para-positions are free in relation to the —OH and —O(CH$_2$)$_n$H groups. It is understood that these numbers for n, b, c, d and x represent average values and an actual hemiformal composition will comprise a equilibrium mixture of various hemiformals of phenol as represented by the above formulas. R is any substituent typically employed in conjunction with a phenolic structure. With respect to R, it is preferably a monovalent radical which includes alkyl of from about 1 to about 18 carbon atoms, cycloalkyl from 5 to 8 carbon atoms, aryl containing from 1 to about 3 aromatic rings, aralkyl, alkaryl, alkoxy containing from 1 to about 18 carbon atoms, aroxy containing 1 to 3 aromatic nuclei, halide such as choride, bromide, fluoride, and iodide; alkyl sulphides having from 1 to about 18 carbon atoms, aryl sulphides having from 1 to about 3 aromatic nuclei, and the like with the proviso that at least 50 mole percent of a hemiformal mixture be unsubstituted with respect to R, i.e. x=0 for 50 mole percent of the hemiformal composition.

The hemiformals shown above are formed by the reaction of formaldehyde with the hydroxyl-group of a phenol to form hemiformals of phenol and/or the reaction with the methylol group of a methylolated phenol to form hemiformals of methylolated phenol. This is accomplished by reacting formaldehyde with liquid phenol and/or with a solution containing methylolated phenol.

The liquid phenols suitable for use in forming hemiformals of phenol useful in the invention are of the formula:

where R and x are defined above and where at least 50 mole percent of the phenol is unsubstituted with respect to R. The substitution with respect to the R substituent should be such that at least two reactive sites on the aromatic ring of the para- and ortho positions in relation to the phenolic hydroxy remain free. The liquid phenol may be in solution with a solvent, that is unreactive to phenols and aldehydes, or be essentially pure molten phenol. Preferably, the phenol is molten phenol. Another source of suitable liquid phenols are those prepared by reacting phenol and an oil such as linseed oil or tung oil in the presence of an acid ion exchange resin. It is well known that these so-called oil-modified phenols comprise complex mixtures containing phenol and various substituted phenols derived from reaction of the phenol with the sites of unsaturation in the carbon-chains of the oils. The resulting substituted or modified phenol mixture can then be treated with formaldehyde as is described herein to produce a hemiformal mixture. In using oil modified phenols to make hemiformals, at least 50 mole percent of the phenol used should be unreacted with the oils.

The suitable methylolated phenols are of the formula:

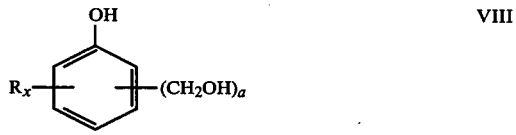

where a is 1 to about 3, R and x are defined above, and the sum of x and a does not exceed 5. Although the methylolated phenols can be isolated and reacted as such with formaldehyde to form hemiformals, they are preferably formed in situ by reacting a liquid phenol, as defined above, and formaldehyde in the presence of a divalent metal catalyst defined below. Thus, hemiformals of methylolated phenol can be formed directly from liquid phenols without isolating the methylolated phenol. Generally, when phenol and formaldehyde are reacted without a divalent metal catalyst essentially no methylolated phenol is formed, the uncatalyzed reaction forming methylol phonols being very slow. Therefore, essentially all of the hemiformals formed in a catalyst-free reaction mixture are formed by reaction of the phenolic hydroxy group and are represented by formula (IV). If a divalent metal catalyst is present in a reaction mixture of phenol and formaldehyde, methylolated phenols are formed. Therefore, both the phenol hydroxy and phenol methylol groups participate in hemiformal production and equilibrium mixtures of hemiformals of Formulas IV, V and VI are formed. Thus the reaction may be carried out catalyst-free to form hemiformals essentially of Formula IV, or be carried out with a divalent metal catalyst to form hemiformals of Formulas IV, V and VI.

The catalyst-free reaction to form hemiformals of Formula IV is preferably carried out by passing gaseous formaldehyde through molten phenol. The molten phenol may be phenol per se or phenol which is oil-modified or substituted with R as characterized above. The gaseous formaldehyde may be obtained from a number of sources. A preferred method of producing gaseous formaldehyde is by heating and decomposing paraformaldehyde into formaldehyde and passing the formaldehyde, free of water, into molten phenol. Another method for producing gaseous formaldehyde is to take the formaldehyde directly as produced by the oxidative decomposition of methanol and introducing the formaldehyde, free of water, to the molten phenol. The reaction between the monomeric or gaseous formaldehyde and the molten phenol takes place at a temperature at which the phenol is molten, such as from melting point of unsubstituted phenol, about 40° C. to about 75° C., preferably about 45° C. to about 60° C.

When using substituted phenols the melting temperature may differ, therefore the reaction temperature may need to be higher to achieve a molten phenol. In any case the temperature should not exceed 75° C.

As stated above it is desirable that the gaseous formaldehyde should be free of water. However, providing formaldehyde which is free of water is quite different to do and in the normal case water will be introduced with the formaldehyde which is provided to the reaction. Usually the amount of water which is tolerable in the practice of this invention is that amount of water which will provide in association with the hemiformal a water concentration of up to about 15 weight percent, based on the total weight of the hemiformal composition. In the preferred embodiment it is desirable that the amount of water which is present in the resultant hemiformal not exceed about 5 weight percent, based on the total weight of the composition.

As described above, the reaction to form essentially only hemiformals of Formula IV does not have to be carried out in the presence of any catalyst and preferably the reaction is carried out in the absence of any catalyst. The typical acidic or basic catalysts which are utilized in the reaction of phenol with formaldehyde to produce resinous structures adversely affect the formation of the hemiformal and their absence from the reaction is highly preferred.

The reaction between the gaseous formaldehyde and the molten phenol is carried out with stirring so as to effect intimate admixture of the reactants and to assure uniform reaction. The reaction may be carried out at subatmospheric or superatmospheric pressures, however, in the usual case one will practice the hemiformal reaction at atmospheric pressure conditions. Since the uncatalyzed reaction between formaldehyde and phenol to make the phenol hemiformal is only mildly exothermic, very little in the way of temperature control is necessary in order to produce the desired hemiformal products.

The reaction carried out in the presence of a divalent metal catalyst to form an equilibrium mixture of hemiformals of formulas IV, V and VI is preferably carried out by reacting essentially water-free paraformaldehyde with molten phenol at a temperature of about 60° C. to 100° C. preferably about 80° C. to about 90° C.

The reaction takes place in the presence of a divalent metal cation such as magnesium, calcium, lead, manganese, strontium, barium, zinc, cadmium or mercury, at a pH of about 3 to 8, preferably from about 4 to 6. Typically, the metal cation is supplied as a salt or as an alkoxide such as a carboxylate salt, or a methoxide or ethoxide of the metal in combination with a mild acid to achieve the desired pH. Suitable salts include the formates, acetates, benzoates, and valerates. Examples of these salts include zinc acetate dihydrate, calcium formate, manganous acetate, lead acetate and zinc benzoate.

The divalent metal catalyst is typically present at a concentration of about 0.2 to 1 weight percent, preferably about 0.4 to about 0.7 weight percent based on the total weight.

The paraformaldehyde can be introduced directly to the liquid phenol. Preferably the paraformaldehyde is water-free.

As stated above it is desirable that the paraformaldehyde be essentially free of water. However, providing a source of paraformaldehyde which is free of water is quite difficult to do and in the normal case water will be carried along with the paraformaldehyde which is provided to the reaction. Usually the amount of water which is tolerable in the practice of this invention is that amount of water which will provide in association with the hemiformal, a water concentration of up to about 15 weight percent, based on the total weight of the hemiformal composition. In the preferred embodiment it is desirable that the amount of water which is present in the resultant hemiformal not exceed about 5 percent, based on the total weight of the hemiformal composition.

The reaction between paraformaldehyde and the molten phenol is carried out with stirring so as to effect intimate admixture of the reactants and the metal catalyst and to assure uniform reaction. The reaction may be carried out at subatmospheric or superatmospheric pressures, however, in the usual case one will practice the hemiformal reaction at atmospheric pressure conditions. Since the catalyzed reactions between formaldehyde and phenol to make phenol hemiformals, methylolated phenols and hemiformals of methylolated phenol, are exothermic, a cooling water bath may be required to maintain the reaction temperature.

The polymers suitable for use in the liquid thermosetting solutions of the invention are of the phenol-formaldehyde resole, phenol-formaldehyde novolac, aromatic polyester, aromatic polycarbonate, unsaturated polyester, poly(aryl-ether), urea-formaldehyde and melamine-formaldehyde type. They must be miscible with the hemiformal and be capable of forming a solution with the hemiformal that has a viscosity low enough to be useful in injection molding or sheet molding compound methods. The viscosity of the hemiformal-polymer solution is preferably less than about 500,000 cps for use in sheet molding compound methods and most preferably less than about 10,000 cps for use in molding methods such as LIM, RIM or RTM. The viscosity depends on the concentration and molecular weight of the polymer or polymers used.

The phenol-formaldehyde resole polymers that can be used in the solutions of the invention include phenolic resins produced by reacting an aldehyde and phenol at an aldehyde to phenol molar ratio equal to or greater than one, generally greater than one, and generally in the presence of an alkaline catalyst. Resoles are generally characterized as compositions that can be cured to a thermoset state by the application of heat without additional aldehyde. The aldehyde component is usually formaldehyde, although not restricted to it. Other aldehydes such as acetaldehyde, furfuraldehyde and the like can replace part or all of the formaldehyde employed in the preparation. Those skilled in the art are fully familiar with resoles, their structure, and methods of manufacture.

The phenol-formaldehyde novolac polymers that can be used in the solutions of the invention are phenolic resins that require additional aldehyde or its equivalent, such as hexamethylenetramine, to cure to a thermoset state. They are produced by reacting an aldehyde and a phenol at an aldehyde to phenol ratio of less than one, usually in conjunction with an acidic catalyst. Those skilled in the art are fully familiar with novolacs, their structure, and methods of manufacture.

The aromatic polyesters useful in the solutions of the invention can be obtained by the condensation of difunctional phenol or mixture of difunctional alcohol and phenol with a dicarboxylic acid. The polymerization is performed in such a way that the resulting polyester contains the phenolic moiety as the terminal group.

unsaturated polyester is structopendant, i.e. the reactive unsaturation is present at an internal rather than at a terminal position and usually the internal unsaturation is alpha to a carbonyl group.

The suitable structopendant unsaturated polyesters are reaction products of maleic anhydride, maleic acid and/or fumaric acid with a difunctional alcohol such as propylene glycol, diethylene glycol, 1,3-butanediol and the like or a dihydroxy phenol such as bis-phenol A, and the like, or hydroquinone and the like. Isophthalic acid and/or terephthalic acid may also be included in the mixture. A preferred unsaturated polyester is a polymer formed by reaction mixture of isophthalic and/or terephthalic acid, maleic acid and/or fumaric acid and a difuncional alcohol of the formula HO-R'-OH where R' is a substituted or unsubstituted alkylene or arylene, said polymer having the repeating unit;

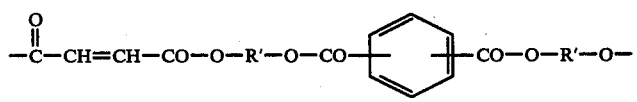

Among the difunctional phenols useful for the preparation of these polyesters one can name hydroquinone, 2,2-bis (4-hydroxyphenyl)propane (bis-phenol A), bis(-hydroxyphenyl)ether, bis(hydroxyphenyl)-thioether, bis(hydroxyphenyl)-methane, bis(hydroxyphenyl)sulfone, and the like. Suitable difunctional alcohols include ethylene glycol, butanediol, hexanediol, cyclohexane dimethanol. Among the suitable dicarboxylic acids are maleic acid, fumaric acid, terephthalic acid, isophthalic acid, naphthalene dicarboxylic acids as well as alkyl substituted homologs of these acids, wherein the alkyl groups contain from 1 to 4 carbon atoms. Other suitable dicarboxylic acids are glutaric acid, adipic acid, suberic acid, azelaic acid, sebacic acid, and dodecane dioc acid.

The aromatic polyesters useful in the compositions of the invention may contain any substituent which will not adversely affect the miscibility or solubility of these polymers in the hemiformal or the subsequent cure of the mixture to a thermoset. Among such substituents one can name halide, hydrocarbyl, alkoxy, ether and thioether.

Illustrative of suitable aromatic polyesters for use in the compositions of this invention one can name bisphenol-A terminated, poly(bisphenol-A iso- or terephthalate), bisphenol-A terminated polyethylene terephthalate, and the like. A preferred aromatic polyester is the poly(bisphenol-A iso-or terephthalate) of the general formula The unsaturated polyesters useful in the compositions of this invention may contain any substituent which will not adversely affect the miscibility of these polymers in the hemiformal or the subsequent cure of the mixture to a thermoset. Among such substituents one can name halide, hydrocarbyl, alkoxy ether and thioether. Preferably the molecular weight is less than 10,000.

The aromatic polycarbonates useful in the invention are polyesters of carbonic acid and a dihydric phenol.

The aromatic polycarbonates are prepared by reacting the dihydric phenol with a carbonate precursor. Typical of some of the dihydric phenols that may be employed are bisphenol-A, bis(4-hydroxyphenyl)-methane, 2,2-bis(4-hydroxy-2-methylphenyl)propane, 4,4-bis(4-hydroxyphenyl)-heptane, (3,3'-dichloro-4,4'-dihydroxydiphenyl)methane, and the like. The terminal group of the dihydric phenol should be a phenol which has at least one para- or orthoposition to the phenolic hydroxy free for reaction with the hemiformal. Other dihydric phenols of the bisphenol type are described in, for example, U.S. Pat. Nos. 2,999,835, 3,028,365 and 3,334,154.

It is, of course, possible to employ two or more different dihydric phenols, or a copolymer of a dihydric phenol with a glycol or with hydroxy or acid terminated polyesters or with a dibasic acid in the event a carbonate copolymer or inter-polymer rather than a homopolymer is derived for use in the preparation of

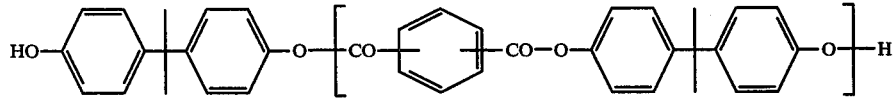

Preferably, the aromatic polyesters should have a molecular weight less than about 10,000.

The unsaturated polyesters useful in the compositions of this invention are well known; these polyesters are characterized by having at least one internal or terminal unsaturation, i.e. —C=C—, which is capable of reacting with a phenol or a methylol phenol compound by an alkylation reaction of the double bond and an ortho- or para- position to the hydroxyl of the benzene ring. Generally, due to availability or ease of preparation, the the aromatic carbonate polymer.

The carbonate precursor may be either a carbonyl halide, a carbonate ester, or a haloformate. The carbonyl halides which can be employed herein are carbonyl bromide, carbonyl chloride and mixtures thereof. Typical of the carbonate esters which may be employed herein are diphenyl carbonate, di(halophenyl)carbonates, such as di-(chlorophenyl)carbonate or di-(bromophenyl)carbonate, etc., di(alkylphenyl)carbonates such as di(tolyl)carbonate, di(naphthyl)carbonate, di(-chloronaphthyl)carbonate, etc. or mixtures thereof. The haloformates suitable for use herein include bis-haloformate of dihydric phenols for example, bischloroformates of bisphenol-A, or hydroquinone, etc. or glycols for example, bishaloformates of ethylene glycol, neopentyl glycol, polyethylene glycol, etc. While other carbonate precursors will be apparent to those skilled in the art, carbonyl chloride, also known as phosgene, is preferred.

The aromatic polycarbonate polymers may be prepared by methods well known in the art by using phosgene or a haloformate and by employing a molecular weight regulator, an acid acceptor and a catalyst. The molecular weight regulators which can be employed in carrying out the process include monohydric phenols, such as phenol, para-tertiarybutylphenol, para-bromophenol, primary and secondary amines, etc. Preferably, a phenol is employed as the molecular weight regulator.

A suitable acid acceptor may be either an organic or an inorganic acid acceptor. A suitable organic acid acceptor is a tertiary amine and includes materials, such as pyridine, triethylamine, dimethylaniline, tributylamine, etc. The inorganic acid acceptor may be one which can be either a hydroxide, a carbonate, a bicarbonate, or a phosphate of an alkali or alkaline earth metal.

The catalysts for making an aromatic polycarbonate can be any of the suitable catalysts that aid the polymerization of, for example, bisphenol-A with phosgene. Suitable catalysts include tertiary amines, such as triethylamine, tripropylamine, N,N-dimethyl-aniline, quaternary ammonium compounds, such as tetraethylammonium bromide, cetyl triethyl ammonium bromide, tetra-n-heptylammonium iodide, and quaternary phosphonium compounds, such as n-butyltriphenylphosphonium bromide and methyl-triphenyl phosphonium bromide.

The aromatic polycarbonates can be prepared in a one-phase (homogeneous solution) or two-phase (interfacial) systems when phosgene or a haloformate are used. Bulk reactions are possible when the diarylcarbonate precursors are used.

The aromatic polycarbonates useful in the compositions of this invention may contain any substituent which will not adversely affect the miscibility of these polymers in the hemiformal or the subsequent cure of the mixture to a thermoset. Among such substituents one can name halide hydrocarbyl, alkoxy, ether, and thioether. The aromatic polycarbonates suitable for use in the invention preferably have a molecular weight less than about 10,000.

The poly(aryl-ether) resin components suitable for use in the invention are linear, thermoplastic polyarylene polyether polysulfones, characterized by arylene units interspersed with ether and sulfone linkages, and by at least one terminal or pendant phenol moiety which is capable of reacting with an aldehyde or methylol phenol compound. These resins may be obtained by reaction of an alkali metal double salt of a dihydric phenol and a dihalobenzenoid compound, either or both of which contain a sulfone or ketone linkage i.e., —SO₂— or —CO— between arylene groupings, to provide sulfone or ketone units in the polymer chain in addition to arylene units and ether units. The polysulfone polymer has a basic structure comprising recurring units of the formula:

—O—E—O—E'— wherein E is the residuum of the dihydric phenol and E' is the residuum of the benzenoid compound having an inert electron withdrawing group in at least one of the positions ortho and para to the valence bonds; both of said residua are valently bonded to the ether oxygens through aromatic carbon atoms. Such polysulfones are included within the class of polyarylene polyether resins described in U.S. Pat. No. 3,264,536 and 4,108,837, for example. A terminal phenol can be obtained by using a stoichiometric excess of the dihydric phenol component so that the terminating group is derived from the dihydric phenol component.

The residuum of a dihydric phenol, E is derived from dinuclear phenols having the structure:

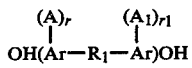

wherein Ar is an aromatic group and preferably is a phenylene group, A and $A_1$ may be the same or different inert substituent groups, such as alkyl groups having from 1 to 4 carbon atoms, halogen atoms, i.e., fluorine, chlorine, bromine or iodine, or alkoxy radicals having from 1 to 4 carbon atoms, r and $r_1$ are integers having a value of from 0 to 4, inclusive, and $R_1$ is representative of a bond between aromatic carbon atoms as in dihydroxydiphenyl, or is a divalent radical, including, for example, CO, O, S, S-S, $SO_2$ or a divalent organic hydrocarbon radical, such as alkylene, alkylidene, cycloalkylene, or the halogen, alkyl, aryl or like substituted alkylene, alkylidene and cycloalkylene radicals as well as alkarylene and aromatic radicals and a ring fused to both Ar groups.

Typical preferred poly(aryl-ether) polymers have recurring units having the following structure:

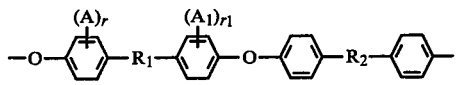

as described in U.S. Pat. No. 4,108,837, supra. In the foregoing formula A and $A_1$ can be the same or different inert substituent groups that will not adversely affect the solubility or miscibility of the polymer in the hemiformal or the subsequent cure to a thermoset. These include alkyl groups having from 1 to 4 carbon atoms, halogen atoms (e.g., . fluorine, chlorine, bromine or iodine) or alkoxy radicals having from 1 to 4 carbon atoms, r and $r_1$ are integers having a value of from 0 to 4, inclusive. Typically, $R_1$ is representative of a bond between aromatic carbon atoms or a divalent connecting radical and $R_2$ represents sulfone, carbonyl, or sulfoxide. Preferably, $R_1$ represents a bond between aromatic carbon atoms. Even more preferred are the thermoplastic polysulfones of the above formula wherein r and $r_1$ are zero, $R_1$ is a divalent connection radical of the formula:

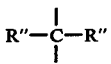

wherein R" is selected from lower alkyl, aryl, and the halogen substituted groups thereof, preferably methyl and $R_2$ is sulfone group.

The most preferred poly(aryl-ether) polymers are polysulfones having the general formula:

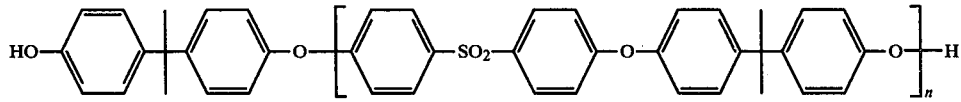

Where n is such that the molecular weight of the poly(aryl ethers) is preferably less than 10,000, most preferably less than 5,000.

The urea-formaldehyde resins useful in the compositions of this invention are produced from the reaction of formaldehyde with the —$NH_2$ groups of the urea. The initial base catalyzed reaction between formaldehyde and urea produces methylol-, dimethylol- and trimethylolureas. This reaction is followed by condensation reactions that eliminate water to form polymers. This mixture of low molecular weight polymers and methylolureas is known as urea-formaldehyde resin which on heating yields insoluble, infusible, crosslinked products. The preparative reactions are illustrated by the idealized structures depicted in the equation below:

$$NH_2CONH_2 + CH_2O \longrightarrow HO-CH_2NH-CO-NH_2 +$$

$$HO-CH_2NH-CONH-CH_2OH +$$

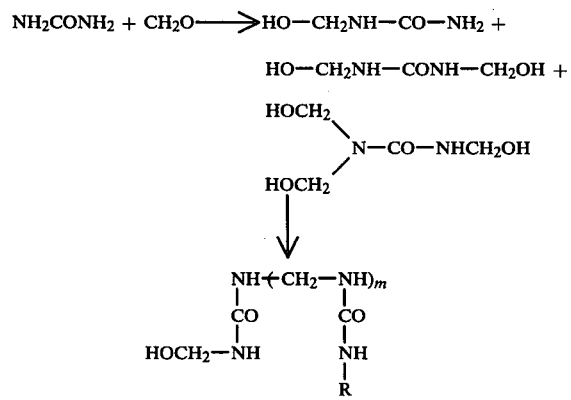

where R is $CH_2OH$ or H.

Preferably the urea-formaldehyde resin are free of volatile solvents such as water, alcohols, and the like.

The melamine-formaldehyde resins useful in the compositions of this invention are produced from the condensation of formaldehyde with the amino groups of melamine (2,4,6-triamino-1,3,5-triazine) generally under basic pH conditions. One mole of the melamine can react with 1–6 moles of formaldehyde yielding mono, di-, tri, tetra-, penta-, and hexamethylolmelamines. These methylol derivatives further polymerize with the elimination of water forming melamines linked by methylene and methylene either bridges. The reaction is illustrated by the following equation:

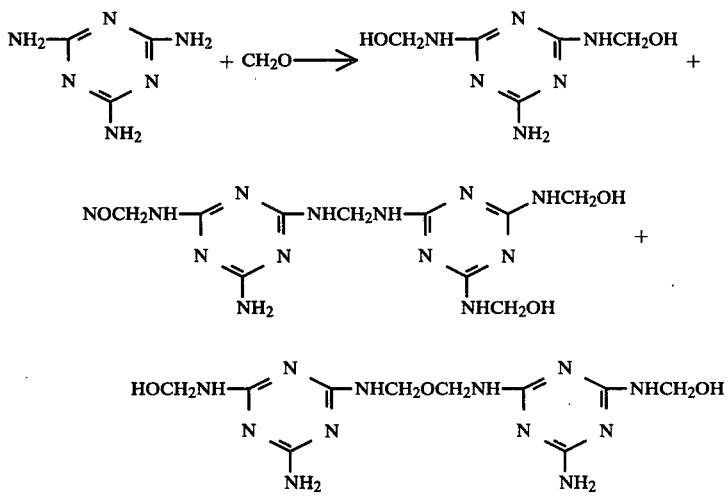

Further condensation of the melamineformaldehyde resin, acelerated by heat or acid catalyst, and especially when tri- to hexamethylolmelamine derivatives are involved yields crosslinked structures.

Preferably the melamine-formaldehyde resins are free of volatile solvents such as water, alcohols and the like.

The compositions of this invention are prepared by admixing the phenol-formaldehyde resole, phenol-formaldehyde novolac, aromatic polyester, aromatic polycarbonate, unsaturated polyester, poly(aryl ether), urea-formaldehyde or melamine-formaldehyde polymer with the phenol hemiformal and/or methylolated phenol hemiformal in the previously described concentrations and in a manner such that a solution is obtained with a viscosity less than about 500,000 centipoise and preferably less than about 10,000 centipoise, depending on the molding method to be used. The admixture may be carried out at any suitable pressure, atmospheric pressure being convenient, and at a temperature of from about ambient temperature (about 20° C.) to about 100° C., preferably from about 60° C. to about 80° C. It is generally advantageous to agitate the mixture vigorously during the preparation to facilitate dissolution. The resulting mixtures comprise the liquid thermosetting compositions of this invention which are curable to thermosets.

The liquid compositions can be cured by the addition of heat. Generally, a catalyst is also added to the composition to enhance the cure rate.

either acids, such as sulfuric and toluene sulfonic acid, or bases, such as organic amines, alkali or alkaline earth hydroxides, can be employed as the aforementioned catalyst. In general, substances which can catalyze phenol/aldehyde condensation reactions can be employed as the catalyst for the curing reaction. The selection of the type and concentration of the catalyst depends on the molding process and the cure rate desired. For example, when employed in a process such as that for sheet molding compounds, wherein the cure of the molding composition is interrupted at some intermediate stage for storage or additional handling, less active catalysts and less vigorous curing conditions would be required. For liquid injection molding or reaction injection molding operations where short cycle time is desired, a more active catalyst and at a higher concentration is of greater utility.

Among the acidic catalysts which have been successfully employed are included phenol sulfonic acid, phosphoric acid, maleic acid, chlorosulfonic acid, toluene sulfonic acid and many others. Phenol sulfonic acid has been found to be quite convenient and is readily obtained by dissolving sulfuric acid in phenol. For processes such as liquid injection molding or reaction injection molding the preferred catalyst is an acidic catalyst at a concentration of about 0.2 to 5 weight percent based on the weight of the uncatalyzed liquid composition. For processes such as sheet molding compounds, the catalyst is preferably a less active catalyst such as basic catalysts like amines at a concentration of up to 10 weight percent based on the weight of the uncatalyzed liquid composition. The actual concentration will depend on the activity of the catalyst used. These catalysts and their activities in phenol/aldehyde condensation reactions are well known in the art.

The preferred curing procedure wherein the catalyst is preferably introduced to the liquid compositions of this invention before the curing step may be termed a one-component system. In such a system the catalyst level is adjusted such that cure is substantially avoided during handling prior to injection into a mold. The mold is at a higher temperature, generally greater than 80° C., so that the curing reaction is activated thermally. Once activated the curing reaction accelerates due to heat evolved by the exothermic reaction.

Another procedure, which may be termed a two-component system, may be employed when one does not wish to keep the composition containing the catalyst in such a state for very long before injection into the mold. In such a two-component system an acidic catalyst is introduced into a solution of phenol and the polymer. This mixture is then pumped and metered into a mixing device concurrently with and separately from the hemiformal such that the components are mixed in the mixing device. After mixing, the liquid composition of this invention which contains a catalyst is injected immediately into a mold where the cure takes place.

The liquid composition of this invention which has had catalyst added thereto, which may be termed a liquid prepolymer, and which may be prepared by either the one or two-component system described above, or any other convenient method, should have a total aldehyde to total phenol molar ratio of from 1:1 to 2:1, preferably from 1.1:1 to 1.8:1, most preferably from 1.2:1 to 1.5:1.

By total aldehyde and total phenol, it is meant the total amount of such moieties existing as free aldehyde or phenol or the equivalent thereof present in the hemiformals or the polymers in the solution. The ratio may be adjusted by addition of a phenol, an aldehyde or additional hemiformal to the prepolymer.

The liquid prepolymer compositions are cured by the application of heat. A temperature of from 80° C. to 200° C., preferably from 120° C. to 160° C., is employed for the cure. The curing time will vary and will depend on such factors as the particular makeup of the thermosetting composition, the temperature, the amount to be cured, the configuration of the cured part, and other factors known to those in the art. Generally curing times are from 1 to 15 minutes. The compositions of this invention cure to hard thermoset plastics.

The liquid compositions of this invention offer many advantages over the prior art because of their stability and low viscosity. These compositions can be handled and conveyed with greater ease and are better suited for use in high speed fabrication techniques such as reaction injection molding.

Other additives may be included in the composites of the invention. These include those commonly used in the above molding methods, such as pigments and various processing aids. Suitable reinforcing agents include carbon/graphite fibers cellulosic fibers such as wood flour, sisal, and organic fibers such as aromatic polyamide. Use of the solutions of the invention to make reinforced composites is disclosed in U.S. patent application Ser. No. 340,695 filed concurrently herewith by Brode, Chow, and Hale.

The following examples serve to further illustrate the invention. They are not intended to limit the invention in any way.

EXAMPLE 1

Methylolated phenol hemiformal was prepared as follows: to a 5 liter reaction flask equipped with a thermometer, stirrer and addition-port there were charged 1410 grams (15 g-moles) of phenol, 742 grams of 91 mole percent paraformaldehyde (paraform) (22.5 g-moles formaldehyde equivalent) and 10.8 grams of zinc acetate dihydrate as catalyst. The mixture was stirred and heated to 85° C. for about 20 minutes. A mild exotherm ensued. The reaction mixture was maintained at from 80° to 90° C. by removal of the external heat source and by occasional cooling with a water bath. After the exotherm subsided, heat was reapplied to maintain a reaction mixture temperature of from 80° to 90° C. until a clear solution was obtained; this took from about 1 to 2 hours. Nuclear magnetic resonance showed the product to be a mixture of hemiformals of phenol and hemiformals of methylolated phenol.

Eight liquid resin compositions were prepared by dissolving various phenol-formaldehyde resole and novolac resins in a hemiformal of methyloated phenol. For runs 1 to 5 the hemiformal prepared above was used. For runs 6 to 8 a hemiformal was used that was prepared in the same manner as above except that 659 grams of 91 weight percent paraformaldehyde (equivalent of 20 moles of formaldehyde), 940 grams phenol (10 moles) and 4.7 grams of zinc acetate dehydrate were used. The resoles had an Inclined Plate Flow of 40–90 mm at 125° C. The novolacs had an Inclined Plate Flow of 60–80 mm when copulverized with 9% hexamethylene-tetramine, based on the total weight of the mixture. The Incline Plate Flow was determined by compressing a one-gram sample of a pulverized product to a pellet 12-13 mm in diameter. This pellet was placed on a glass plate and heated for three minutes in a 125° C. oven. The plate was then tilted to a 60° angle and heating continued for an additional 20 minutes. The distance, measure in mm, the resin travelled is known as the Inclined Plated FLow.

The hemiformal was heated to about 50° C. to 70° C. and agitated as the polymer was added. In Table I are shown the formaldehyde to phenol ratio of the hemiformal used, the polymer type and its form, the comparative percentages of the hemiformal and polymer in the liquid thermosetting composition, and the Brookfield viscosity of the liquid thermosetting composition for each run.

EXAMPLE 2

Liquid resins prepared in Example 1 were cured and used to form reinforced composites by the following procedure. A reactive liquid prepolymer was prepared by adding a solution of phenol and sulfuric acid to a liquid resin of Example 1 to form a liquid prepolymer containing phenol sulfonic acid. The added phenol to sulfuric acid weight ratio was 9. The weight percent, of the added phenol-sulfuric acid catalyst, based on the total liquid prepolymer, is shown in Table II, as are the particular liquid resins from Example I that were used.

EXAMPLE 3

Eleven liquid thermosetting compositions were prepared by dissolving various polymers in hemiformal compositions.

The hemiformals were prepared as follows:

(a) Preparation of a Phenol Hemiformal

Monomeric formaldehyde was generated by the pyrolysis of paraform as follows. A slurry of 200 grams of commercial 95% paraformaldehyde in 500 ml of mineral oil was charged into a 2 liter flask which was equipped with a stirrer, thermometer, gas inlet and outlet tubes. The mixture was heated at 120° C.-140° C. under a nitrogen atmosphere. The gaseous formaldehyde formed was swept by a stream of nitrogen via heated connected glass tubes through a cold trap (−20° C.) and then fed to 400 grams of molten phenol. Additional paraform in 100 gram portions was added to the mineral oil as it was being depleted by the pyrolysis. The formaldehyde concentration in the hemiformal was determined as follows. ABout 1-1.5 grams of hemiformal was stirred in about 75 ml of methanol and adjusted to a pH of 4.0. One normal (1 N) hydroxylamine hydrochloride solution (75 ml), also at pH 4.0 was added to the methanol solution and allowed to react for about 1 hour.

TABLE II

| Composite No. | Liquid Resin Composition from Run | Catalyst (wt. %) | Mold Temp. (°C.) | Cure Time (min.) | Fiberglass (Vol. %) | Fiberglass (wt. %) | Thermoset (wt. %) |
|---|---|---|---|---|---|---|---|
| 1 | 4 | 0.04 | 120-150 | 15 | 46 | 65 | 35 |
| 2 | 4 | 0.04 | 140-160 | 14 | 47 | 66 | 34 |
| 3 | 4 | 0.04 | 150 | 10 | 33 | 52 | 48 |
| 4 | 5 | 0.03 | 147-150 | 10 | 24 | 40 | 60 |
| 5 | 4 | 0.04 | 150 | 11 | 21 | 36.5 | 63.5 |
| 6 | 1 | 0.1 | 120-150 | 8 | 45 | 63.6 | 36.4 |
| 7 | 1 | 0.1 | 120-150 | 10 | 31 | 49 | 51 |
| 8 | 1 | 0.1 | 120-150 | 8 | 20 | 35 | 65 |
| 9 | 4,6 | 0.04 | 120-155 | 13 | 49 | 67 | 33 |
| 10 | 4,6 | 0.04 | 110-150 | 14 | 43 | 62 | 38 |
| 11 | 4,6 | 0.04 | 140-153 | 10 | 21 | 37 | 63 |
| 12 | 4,6 | 0.04 | 120-150 | 12 | 21 | 36.4 | 63.6 |
| 13 | 4,6 | 0.04 | 110-150 | 16 | 35 | 53.6 | 46.4 |

The catalyzed mixture was then charged into a mold containing a fiber-glass mat. The Fiber-glass mat was type AKM available from PPG Industries, Inc., Pittsburgh, Pa. The mold was placed in a press and heated to curing temperature.

The solution was then titrated with a standardized 0.5 N sodium hydroxide to a pH 4.0. The resulting hemiformal contained the equivalent of 34.4% formaldehyde which corresponds to a phenol/formaldehyde ratio of 1.6:1.

TABLE I

| Run | Formaldehyde/Phenol Mole Ratio In Hemiformal | Polymer Type | Liquid Resin Composition Hemiformal (wt %) | Liquid Resin Composition Polymer (wt %) | Viscosity Brookfield cps, °C. |
|---|---|---|---|---|---|
| 1 | 1.5 | Resole, lumps | 70 | 30 | 1,500, 40° C. |
| 2 | 1.5 | Resole, lumps | 60 | 40 | 5,000, 40° C. |
| 3 | 1.5 | Resole, lumps | 50 | 50 | 20,000, 40° C. |
| 4 | 1.5 | Resole, powder | 70 | 30 | 1,150, 50° C. |
| 5 | 1.5 | Resole, powder | 60 | 40 | — |
| 6 | 2.0 | Novolac, flakes | 70 | 30 | 540, 50° C. |
| 7 | 2.0 | Novolac, flakes | 60 | 40 | 1,300, 50° C. |
| 8 | 2.0 | Novolac, flakes | 50 | 50 | 6,800, 50° C. |

The temperature ranges of the cure and the curing times are shown in Table II. The content of fiberglass in weight and volume percent and the content of thermoset composition in the cured composites are also shown. In Runs 9 to 13 equal amounts by weight of the resins prepared in Runs 4 and 6 of Example 1 were used.

Five other phenol hemiformals were prepared in the same manner as above, were similarly analyzed and found to have formaldehyde to phenol molar ratios of 1.75, 1.87, 1.65, 1.48 and 1.73.

(b) Preparation of a Phenol/p-Cresol Hemiformal

Gaseous formaldehyde was generated by the method described in (a) above and was fed into a mixture of 54 grams of p-cresol and 141 grams of phenol at 40°–60° C. The hemiformal was analyzed for formaldehyde by the method in (a) and was found to contain an equivalent of 34.7% formaldehyde corresponding to a formaldehyde to phenol-p-cresol molar ratio of 1.71:1.

(c) Preparation of a Hemiformal of Linseed Oil-Modified Phenol

Linseed Oil-modified phenol was prepared by mixing in a three-necked flask equipped with a stirrer 69.5 grams of Linseed Oil, 188 grams of phenol and 2 grams of an acidic ion exchange resin (Amberlyst A-15) for 4 hours at 150° C. The ion exchange resin was then removed from the linseed oil-modified phenol by filtration.

Gaseous formaldehyde was prepared as in (a) above and fed into the modified phenol at 45°–65° C. The resulting hemiformal was analyzed as in (a) above and found to contain the equivalent of 27 percent formaldehyde, corresponding to a formaldehyde to modified phenol molar ratio of 1.6:1.

(d) Preparation of a Hemiformal of Tung Oil-Modified Phenol

Tung Oil-Modified phenol was prepared by mixing together in a three-necked flask equipped with a stirrer 52 grams of Tung Oil; 188 grams of phenol and an acid ion exchange resin (Amberlyst 15) for 3 hours at 100° C.

To prepare the hemiformal, gaseous formaldehyde prepared as in (a) was fed into the modified phenol at 45°–65° C. The resulting hemiformal of tung oil-modified phenol was analyzed as in (a) and found to contain the equivalent of 40 percent formaldehyde which corresponds to a formaldehyde to modified phenol molar ratio of 2.7:1.

The polymers used in the thermosetting compositions of this example were prepared and characterized as follows:

(e) Preparation of Unsaturated Polyester

A solution of 2,2-dimethyl-3-hydroxypropyl 2,2-dimethyl-3-hydroxy-propionate (224.7 grams, 1.1 moles), fumaryl chloride (76.6 g, 0.5 mole) and 150 isophthaloyl chloride (101.5 grams, 0.5 mole) in 1 liter of anhydrous trichlorobenzene was heated at reflux while a stream of nitrogen was sparged through to displace the hydrogen chloride evolved. After about 18 hours, at reflux, the evolution of hydrogen chloride ceased; the unsaturated polyester was recovered by evaporating the solvent under reduced pressure.

(f) Preparation of Aromatic Polyester

A mixture of 31.25 grams (0.3) mole) of neopentyl glycol, 152.3 grams (0.75 g-mole of isophthaloyl chloride and 50.76 grams (0.25 g-mole) terephthaloyl chloride in 3 liters of anhydrous trichlorobenzene was stirred at reflux. The hydrogen chloride liberated was sparged from the reaction mixture with a stream of nitrogen. When hydrogen chloride evolution cease, which was about 2–3 hours, 171.3 grams (0.75 mole) of bisphenol-A was added. Heating and sparging with nitrogen was continued until no more hydrogen chloride was evolved. The solution was cooled and the polyester recovered by coagulation in methanol had a reduced viscosity (in p-chlorophenol at 50° C.) of 0.2 dl/g. The aromatic polyester thus formed had the phenol moiety in the terminal position.

(g) The Novolac Phenolic Resin

The novolac resin was a commercial resin having an Inclined Plate Flow of 60–80 mm when containing 9 weight percent, based on the total weight of the composition, of hexamethyleneltramine.

Various solutions of the above described hemiformals with the novolac resins in (g) were prepared by stirring the hemiformal at about 80° to 85° C. while adding the pulverized novolac resin in small portions over 15–30 minutes. The stirring was continued until a solution resulted; this took an additional 15–30 minutes. The composition was then cooled to room temperature.

Various solutions of the above described hemiformals with the aromatic polyesters of (f) and the unsaturated polyester of (e) were prepared by vigorously stirring 319 grams of hemiformal at 60° to 70° C. and adding an amount of polyester over 1 hour to give solutions of the compositions shown in Table V. Solutions having two different polymers were made by dissolving appropriate amounts of each polymer individually as described above. The solutions were then cooled to room temperature.

In Table III are summarized the eleven thermosetting compositions that were prepared.

TABLE III

| Composition No. | Hemiformal Type | Hemiformal Wt % | Hemiformal Formaldehyde/phenol Mole Ratio | Polymer Type | Wt % |
|---|---|---|---|---|---|
| 9 | phenol | 70.6 | 1.75 | aromatic polyester | 29.4 |
| 10 | phenol | 70 | 1.87 | aromatic polyester | 30 |
| 11 | phenol | 50 | 1.65 | novolac | 50 |
| 12 | phenol | 66.1 | 1.48 | unsat. polyester | 16.95 |
|   |   |   |   | novolac | 16.95 |
| 13 | phenol | 66.1 | 1.73 | unsat. polyester | 16.95 |
|   |   |   |   | novolac | 16.95 |
| 14 | phenol | 66.1 | 1.73 | novolac | 33.9 |
| 15 | phenol (72.3 wt %) p-cresol (27.7 wt %) | 66.7 | 1.7 | unsat. polyester novolac | 16.95 16.95 |
| 16 | phenol (73 wt %) oil, linseed (27 wt %) | 50 | 1.6 | novolac | 50 |
| 17 | phenol (78.3 wt %) tung oil (21.7 wt %) | 50 | 2.7 | novolac | 50 |
| 18 | phenol (1) | 66.1 | 1.6 | novolac unsat. polyester | 16.95 |
| 19 | phenol (2) | 66.1 | 1.6 | novolac | 16.95 |

TABLE III-continued

| Composition No. | Hemiformal Type | Hemiformal Wt % | Hemiformal Formaldehyde/phenol Mole Ratio | Polymer Type | Wt % |
| --- | --- | --- | --- | --- | --- |
| | | | | unsat. polyester | 16.95 |

(1) contains 7 wt % ethylene glycol as viscosity reducer
(2) contains 7 wt % diethylene glycol as viscosity reducer Shown are the weight percent, based on the total weight of the composition, of the specific hemiformals and polymers in each thermosetting composition.

EXAMPLE 4

The eleven thermosetting compositions prepared in Example 3 were formulated into cured glass-fiber reinforced composites.

To Compositions 9, and 11 to 19 hexamethylenetetramine (hexa) was mixed with the liquid thermosetting composition to supply additional formaldehyde and to act as a catalyst by the release of ammonia. To Composition 10 no hexa was added, and sodium hydroxide was added as a catalyst. The mixtures were then poured into reinforcing glass fiber. The glass fiber was AKM type non-woven mats, available from PPG Industries, Inc., Pittsburgh, Penn. The mixtures were gradually heated at about 60° to 160° C. for about 15 minutes to yield a partially cured tack-free composition (B-staged). The B-staged compositions were then charged into a mold and completely cured. In Table VI are shown that weight percent hexa or NaOH present in the mixture, the content of glass fiber in weight percent, the conditions of the second curing step, the cure time and the mold temperature.

EXAMPLE 5

A composition having a pasty consistency comprising 60 grams of a phenol hemiformal-resole liquid reactive composition made as in Example 1, 3 grams of calcium oxide catalyst, 17 grams of calcium carbonate filler and 20 grams of chopped glass fiber was squeezed into a sheet about ⅛ inch thick between layers of polyethylene film and then heated at 100° C. for 20 minutes in a circulating air oven. (The glass fiber was ¼" chopped glass, Type 1156 available from PPG Industries, Inc., Pittsburgh, Penn.) A soft, malleable sheet was obtained which remained malleable for over 3 months storage. The completely cured composite was obtained by compression molding at 150° to 175° C. for 5 minutes.

TABLE VI

| Composition | Hexa or NaOH (Wt %) | Mold Temp (°C.) | Cure Time (Min) | Fiberglass (Wt %) |
| --- | --- | --- | --- | --- |
| 9  | 1.8  | 140–150 | 45 | 30 |
| 10 | 0.3* | 200     | 20 | 20 |
| 11 | 1.0  | 140–155 | 15 | 38 |
| 12 | 1.0  | 140–155 | 15 | 40 |
| 13 | 1.0  | 160     | 25 | 50 |
| 14 | 1.0  | 150     | 20 | 38 |
| 15 | 1.5  | 150–155 | 60 | 31 |
| 16 | 1.0  | 160     | 30 | 34 |
| 17 | 1.0  | 140     | 15 | 30 |
| 18 | 1.0  | 150     | 25 | 64 |
| 19 | 1.0  | 150–155 | 25 | 57 |

*NaOH catalyst.

What is claimed is:

1. A liquid solution curable to a thermoset resin which comprises;

(I) From 40 to 80 weight percent, based on the total weight of the solution, of a hemiformal composition of a phenol having any one of the formulas:

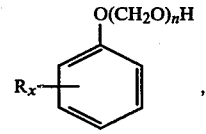

or

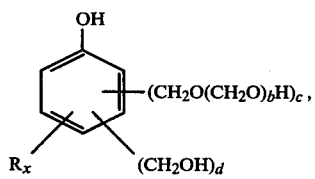

or

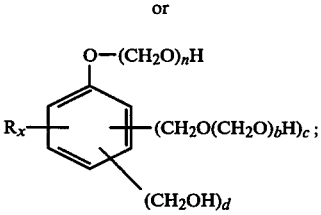

wherein n is a positive number of greater than 1, b is 1 to about 5, and c is 1 to about 3, d is 0 to about 2, the sum of c and d is at least 1 and no greater than 3, the sum of c, d and x is at least 1 and no greater than 5, x is 0 to 3, R is a monovalent radical wherein x=0 for at least 50 weight peercent, based on the hemiformal composition, of the hemiformal composition; and (II) from 20 to 60 weight percent, based on the total weight of the solution, of a polymer capable of forming solution with the hemiformal composition of (I), said polymer being from the group; phenol-formaldehyde resoles, phenol formaldehyde novolacs, aromatic polyesters, aromatic polycarbonates, unsaturated polyesters, aromatic polyethers, urea-formaldehyde resins and melamine-formaldehyde resins.

2. A liquid solution as in claim 1 where (I) is present in a concentration of from 50 to 70 weight percent and (II) is present in a concentration of from 30 to 50 weight percent.

3. A liquid solution as in claim 1 having a viscosity less than 500,000 centipoise at 25° C.

4. A liquid solution as in claim 1 having a viscosity less than 10,000 at 25° C.

5. A liquid solution as in claim 1 having a total aldehyde to total phenol molar ratio of from 1:1 to 2:1.

6. A liquid solution as in claim 1 having a total aldehyde to total phenol molar ratio of from 1.1:1 to 1.8:1.

7. A liquid solution as in claim 1 having a total aldehyde to total phenol molar ratio of from 1.2:1 to 1.5:1.

8. A liquid solution as in claim 1 wherein component (I) is the reaction product of an oil-modified phenol and a formaldehyde.

9. A liquid solution as in claim 8 wherein the oil-modified phenol is linseed oil-modified phenol.

10. A liquid solution as in claim 9 wherein the oil-modified phenol is tung oil-modified phenol.

11. In a liquid injection molding process for the formation of thermosets which comprises injection of a liquid thermosetting resin into a mold, the improvement wherein the liquid thermosetting resin comprises;

(I) From 40 to 80 weight percent, based on the total weight of the solution, of a hemiformal composition of a phenol having any one of the formulas:

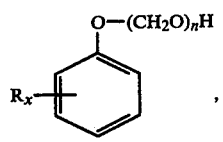

or

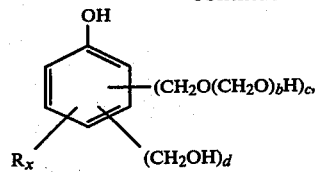

or

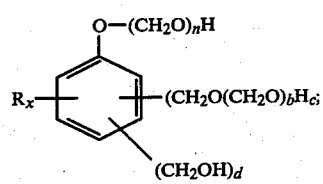

wherein n is a positive number of at least 1, b is 1 to about 5, and c is 1 to about 3, d is 0 to about 2, the sum of c and d is at least 1 and no greater than 3, the sum of c, d and x is at least 1 and no greater than 5, x is 0 to 3, R is a monovalent radical wherein $x=0$ for at least 50 weight percent, based on the hemiformal composition, of the hemiformal composition; and (II) from 20 to 60 weight percent, based on the total weight of the solution, of a polymer capable of forming solution with the hemiformal composition of (I), said polymer being from the group; phenol-formaldehyde resoles, phenol formaldehyde novolacs, aromatic polyesters, aromatic polycarbonates, unsaturated polyesters, poly(aryl-ethers), urea-formaldehyde resins and melamine-formaldehyde resins.

* * * * *